(12) United States Patent
Bernard et al.

(10) Patent No.: US 6,964,687 B1
(45) Date of Patent: Nov. 15, 2005

(54) ANATOMICAL INTERBODY IMPLANT AND GRIPPER FOR SAME

(75) Inventors: Pierre M. Bernard, Bordeaux (FR); Vincent Pointillart, Bordeaux (FR)

(73) Assignee: Scient'x, Guyancourt (FR)

(*) Notice: Subject to any disclaimer, the term of this patent is extended or adjusted under 35 U.S.C. 154(b) by 139 days.

(21) Appl. No.: 10/030,398

(22) PCT Filed: Jul. 7, 2000

(86) PCT No.: PCT/FR00/01967

§ 371 (c)(1),
(2), (4) Date: Sep. 12, 2002

(87) PCT Pub. No.: WO01/03615

PCT Pub. Date: Jan. 18, 2001

(30) Foreign Application Priority Data

Jul. 9, 1999 (FR) .................................. 99 09122

(51) Int. Cl.[7] .............................................. A61F 2/44
(52) U.S. Cl. ................................ 623/17.16; 623/17.11
(58) Field of Search ........................... 623/17.11, 17.16

(56) References Cited

U.S. PATENT DOCUMENTS

| | | | |
|---|---|---|---|
| 5,683,464 A | 11/1997 | Wagner et al. | |
| 5,865,845 A | 2/1999 | Thalgott | |
| 5,888,222 A * | 3/1999 | Coates et al. | 623/17.16 |
| 5,888,227 A * | 3/1999 | Cottle | 623/17.16 |

FOREIGN PATENT DOCUMENTS

| | | |
|---|---|---|
| FR | 2703580 | 10/1994 |
| FR | 2727003 | 5/1996 |
| FR | 2747034 | 10/1997 |
| WO | WO 9848738 | 11/1998 |

* cited by examiner

Primary Examiner—Thomas Barrett
(74) Attorney, Agent, or Firm—Ladas & Parry LLP

(57) ABSTRACT

The invention relates to an intersomatic implant designed to be inserted in the disk space defined between two adjacent vertebrae, namely an overlying vertebra and an underlying vertebra, for the purpose of reestablishing the anatomic space between the vertebrae, the implant being in the form of a cage (1) that is generally in the shape of a rectangular block having at least two sagittal walls (2, 3) interconnected at least by an anterior transverse wall (4) and by a posterior transverse wall (5), the walls (2 to 5) presenting rims (10) extending on one surface to define a first transverse face (8) and on the other side to define a second transverse face (9).

According to the invention, the implant comprises:
a first transverse face (8) presenting in the sagittal plane a convex profile congruent with the sagittal anatomic profile of an overlying vertebra; and
a second transverse face presenting in the frontal plane a convex profile congruent with the frontal anatomic profile of an overlying vertebra.

7 Claims, 3 Drawing Sheets

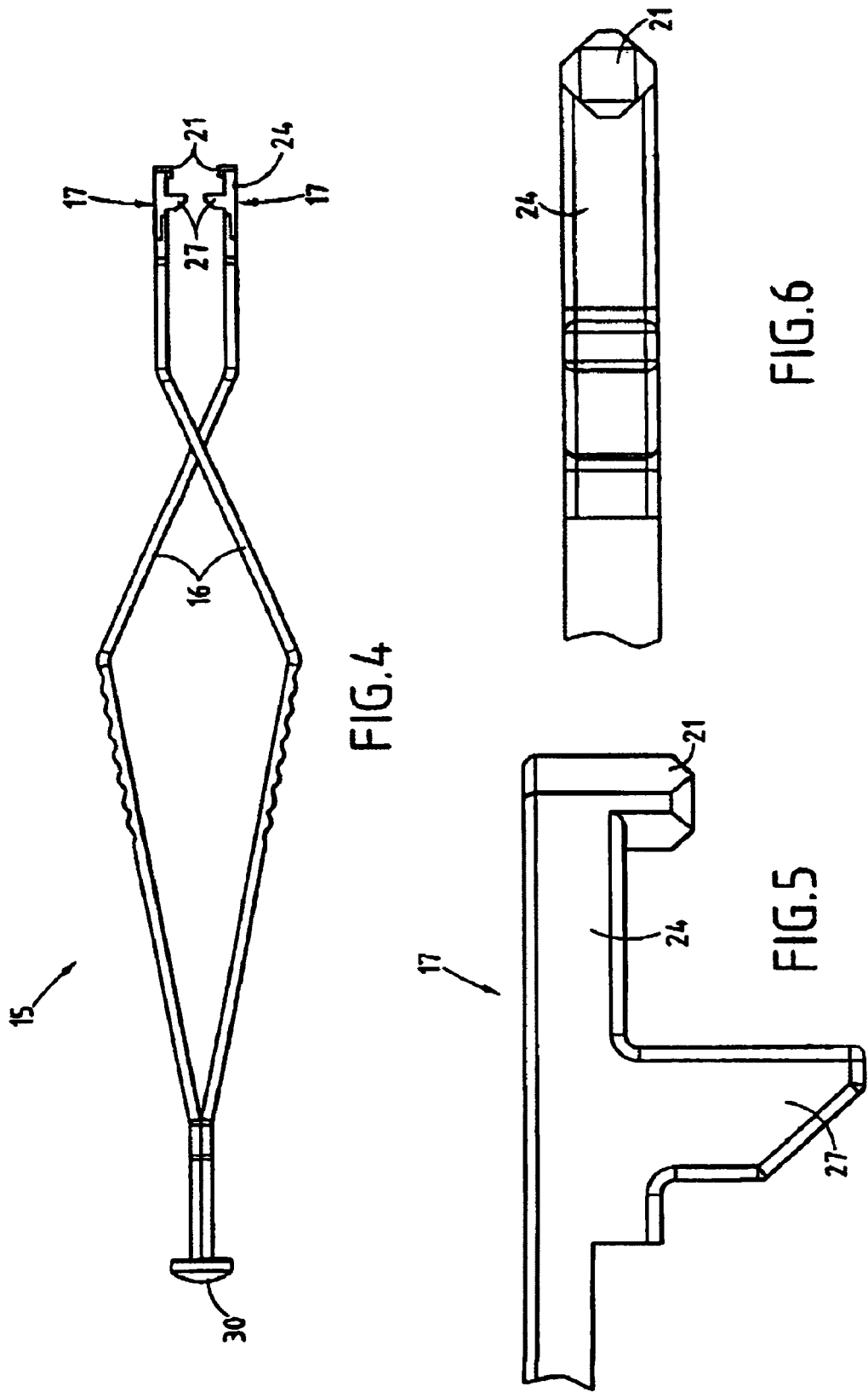

US 6,964,687 B1

ANATOMICAL INTERBODY IMPLANT AND GRIPPER FOR SAME

TECHNICAL FIELD

The present invention relates to an intersomatic implant for insertion into the disk space defined between two adjacent vertebrae, in order to restore an appropriate height between the vertebrae and in order to allow bone fusion to take place between said adjacent vertebrae.

More precisely, the invention provides an intersomatic implant of the cervical type, for insertion into the disk space defined between two adjacent cervical vertebrae.

PRIOR ART

In the state of the art, it is known to insert an intersomatic implant into the disk space between defined between two adjacent cervical vertebrae. Numerous embodiments of such intersomatic implants are proposed in the prior art. For example, a known cervical intersomatic implant is in the form of a cage comprising two sagittal walls interconnected by a anterior transverse wall and by a posterior transverse wall. Between them, the walls define an open volume for receiving a bone-filler substance for encouraging bone fusion between the two vertebrae.

In general, it can be assumed that inserting an implant of the above-described type into the disk space between two adjacent vertebrae is liable to lead to the vertebrae being incorrectly positioned relative to each other. This means that it is not possible to obtain good bone reconstitution between the vertebrae concerned.

The invention thus seeks to remedy the above-specified drawbacks by proposing an intersomatic implant adapted to comply better with the anatomy of the spinal column.

SUMMARY OF THE INVENTION

To achieve such an object, the intersomatic implant is designed to be inserted into the disk space defined between two adjacent vertebrae, namely an overlying vertebra and an underlying vertebra, for the purpose of reestablishing the anatomic space between the vertebrae, the implant being in the form of a cage that is generally in the shape of a rectangular block having at least two sagittal walls substantially parallel to a sagittal plane and interconnected at least by an anterior transverse wall and by a posterior transverse wall extending substantially parallel to a frontal plane, the walls defining between them an open volume for bone filler and presenting rims extending on one surface to define a first transverse face and on the opposite surface to define a second transverse face.

According to the invention, the implant comprises:
  a first transverse face presenting in the sagittal plane a convex profile congruent with the sagittal anatomic profile of an overlying vertebra; and
  a second transverse face presenting in the frontal plane a convex profile congruent with the frontal anatomic profile of an overlying vertebra.

The invention also seeks to provide an instrument for manipulating such a cage, enabling the drawbacks of known manipulation instruments to be remedied. It is known to provide two holes in the anterior wall of a cage so as to enable two fingers presented by a manipulation instrument to be engaged therein. Unfortunately, while the instrument is manipulating the cage, there is a risk of the cage becoming separated from the instrument, and of it becoming impossible to withdraw the implant after it has been put into place.

Another object of the invention is thus to provide an instrument for manipulating a cage in the general sense, regardless of whether it is cervical and/or lumbar, and adapted to hold the implant safely and reliably while it is being put into place or repositioned.

To achieve such an object, the manipulation instrument of the invention is a forceps for an implant in the form of a cage generally in the shape of a rectangular block comprising at least two sagittal walls substantially parallel to a sagittal plane and interconnected at least by an anterior transverse wall and by a posterior transverse wall substantially parallel to a frontal plane, the cage being provided with two housings extending substantially facing each other in a frontal direction substantially perpendicularly to the sagittal plane of the cage, the forceps having two branches movable relative to each other and each provided with an insert-engaging jaw.

According to the invention, each jaw is provided with a radial stud extending in line with the other radial stud and suitable for being moved towards the other stud so so as to be engaged in a respective housing formed in the implant.

Various other characteristics appear from the following description given with reference to the accompanying drawings which show embodiments and implementations of the invention as non-limiting examples.

BRIEF DESCRIPTION OF THE DRAWINGS

FIG. 4 is a plan view of a forceps for manipulating an implant in accordance with the invention.

FIGS. 5 and 6 are views on a larger scale respectively from above and from the side showing the implant-engaging jaws of the forceps shown in FIG. 4.

BEST METHOD OF IMPLEMENTING THE INVENTION

Figure 1:
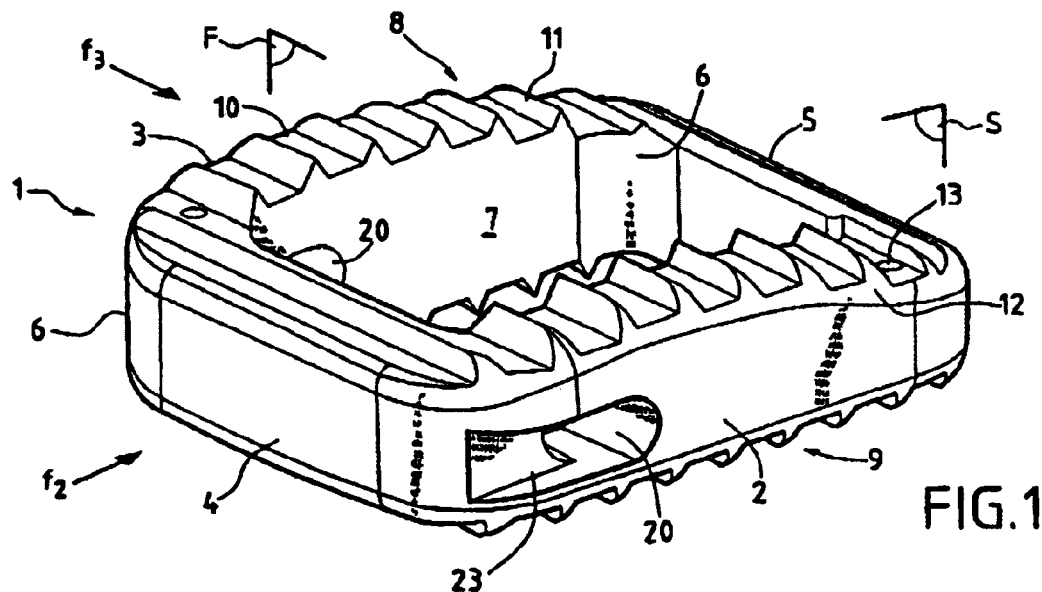
FIG. 1 is a perspective view of an embodiment of an implant in accordance with the invention.
Figure 2:
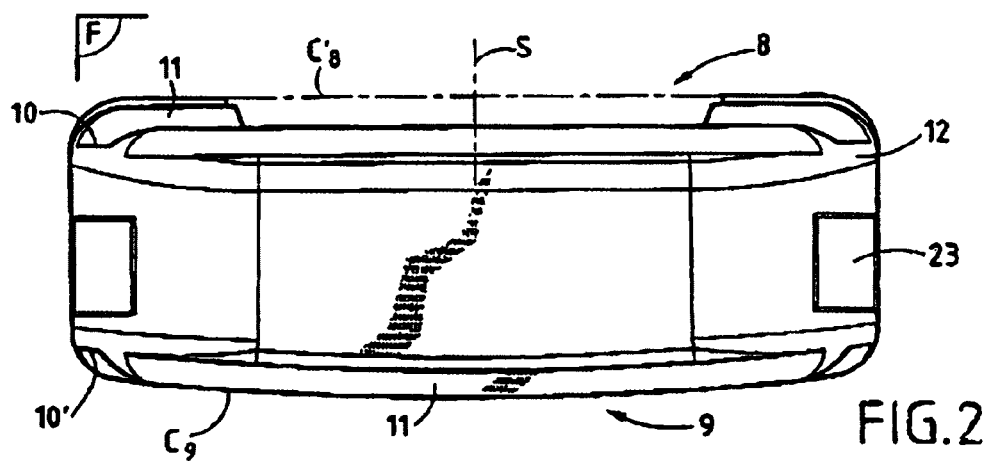
FIG. 2 is a front view of an implant seen substantially along arrows $f_2$ of FIG. 1.
Figure 3:
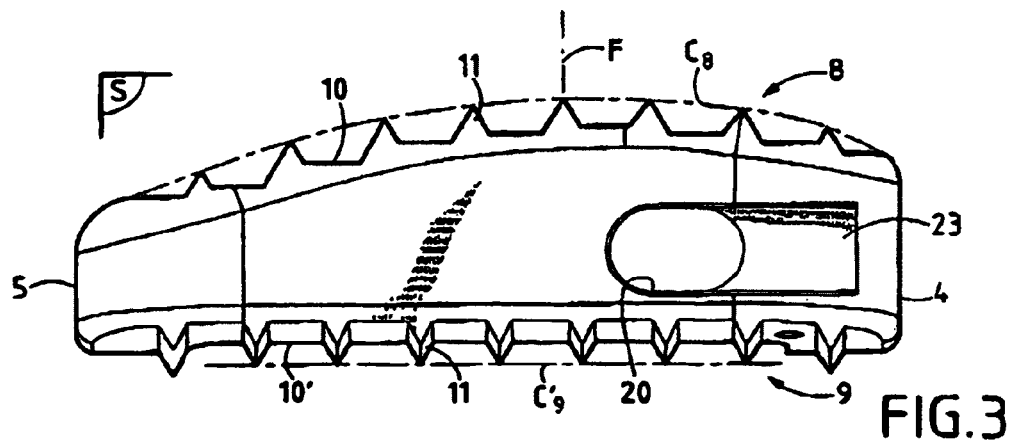
FIG. 3 is a sagittal view of an implant seen substantially along arrow $f_3$ of FIG. 1.
Figure 7:
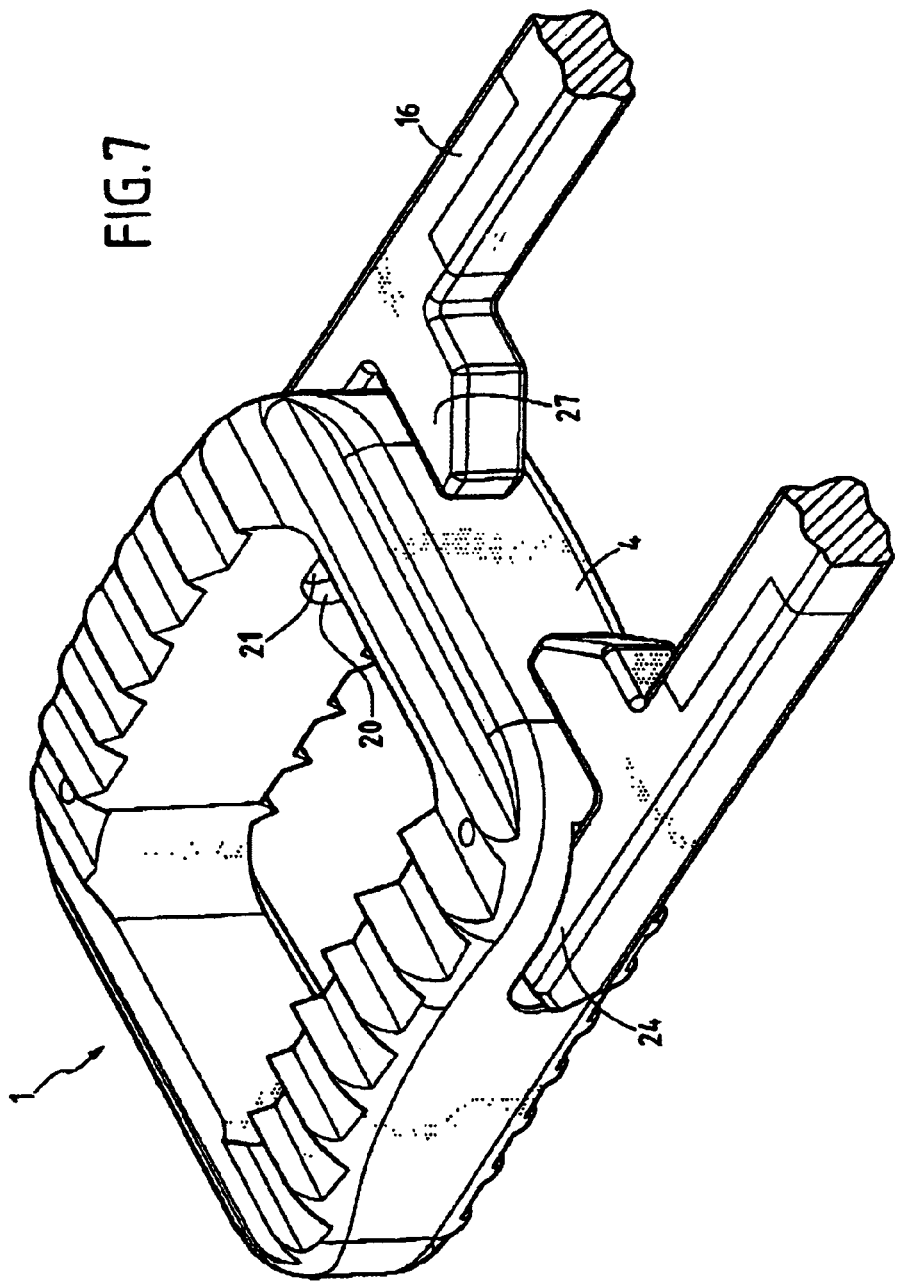
FIG. 7 is a perspective view showing an intersomatic implant supported by a manipulation forceps in accordance with the invention.

As can be seen more precisely in FIGS. 1 to 3, an intersomatic implant in accordance with the invention is in the form of a cage 1 which is generally in the form of a rectangular block and is designed to be inserted in the disk space between two adjacent vertebrae, e.g. cervical vertebrae. The cage 1 has a first sagittal wall 2 and a second sagittal wall 3 extending substantially parallel to each other and to a "sagittal" or "antero-posterior" plane S. The sagittal walls 2 and 3 are interconnected by an "anterior" transverse wall 4 and by a "posterior" transverse wall 5 extending parallel to each other and to a frontal plane F extending perpendicularly to the sagittal plane S.

It should be observed that the cage 1 can have one or more intermediate or mid walls extending substantially parallel to the sagittal and/or transverse walls. Preferably, connecting fillets 6 are provided between the sagittal walls and the transverse walls firstly along their internal vertical faces and secondly along their external vertical faces so as to provide a cage 1 having rounded corners on its external and internal vertical faces. For example, the walls 2 to 5 present substantially the same thickness. Similarly, the height of the anterior transverse wall 4 is greater than the height of the posterior transverse wall 5 (FIG. 3).

Internally, the cage 1 presents a volume 7 defined by the vertical inside faces of the walls 2 to 5 and designed to be filled with a bone-filler substance for prompting intersomatic fusion. In the example shown, this volume 7 opens out into a first transverse face 8 that is on top and into a second transverse face 9 that is at the bottom. The walls 2 to 5 present, on one surface, rims 10 defining the top transverse face 8, and on the opposite surface, rims 10' defining the bottom transverse face 9.

The cage 1 has protuberances or projections 11 formed on the rims 10 and 10' of the walls 2 to 5 so as to enable the cage to bite into the underlying and overlying vertebrae. In the preferred example shown, the protuberances 11 are constituted by ridges extending parallel to one another and to the frontal plane F. Naturally, the protuberances can be of different shapes and could be implemented, for example, in the form of individual spikes or by ridges forming chevrons. In general, it should be understood that the top and bottom transverse faces 8 and 9 correspond to the envelope containing the tips of the protuberances 11.

According to a characteristic of the invention which is shown more clearly in FIG. 3, the top transverse face 8 has a convex profile $C_8$ in the sagittal plane S which is congruent with or complementary to the sagittal anatomic profile of an adjacent or overlying vertebra in the example shown. It should be understood that the rims 10 of the walls and more precisely the protuberances 11 defining said top transverse face 8 are arranged to be inscribed in an envelope whose section in the sagittal plane S is rounded or convex in shape.

In a preferred embodiment, the top transverse face 8 is defined in the frontal plane F by a straight or rectilinear profile $C'_8$ (FIG. 2). The rims 10 of the walls 2 to 5 defining the top transverse face 8 are preferably arranged to be connected to the outside faces of the walls 2 to 5 via connecting fillets 12.

According to another characteristic of the invention which can be seen more clearly in FIG. 2, the bottom transverse face 9 presents a convex profile $C_9$ in the frontal plane F, which profile is congruent with or complementary to the frontal anatomic profile of an adjacent or underlying vertebra in the example shown. The rims 10' of the walls 2 to 5, and more precisely the protuberances 11 defining said transverse face 9 are arranged to be inscribed in an envelope whose section in the plane S is of rounded shape.

Furthermore, it should be observed that the bottom transverse face 9 presents a profile $C'_9$ in the sagittal plane that is substantially straight.

Advantageously, the above-described cage 1 is adapted to receive at least one, and in the example shown two, radio-opaque markers 13 incorporated over at least a portion of the height of the cage in the anterior and posterior transverse walls 4 and 5.

The above-described cage 1 is particularly adapted to enable it to be manipulated by manipulation forceps 15 of the kind shown in FIGS. 4 to 7, the forceps having two branches 16 each provided at one end with an insert-engage jaw 17.

The cage 1 has two housings 20 extending in line with each other and each adapted to receive a radial stud 21 formed on each of the jaws 17 of the forceps. In the example shown, the housings 20 are formed in the sagittal walls 2 and 3, being in alignment and extending in a frontal direction perpendicular to the sagittal plane S. The housings 20 are preferably located close to the anterior transverse wall 4. In the example shown, each housing 20 opens out into the two opposite vertical faces of the walls 2 and 3. Naturally, the housings 20 could be provided in the anterior transverse wall 4 extending in a frontal direction perpendicular to the sagittal plane S. In this embodiment, it can be observed that the two housings 20 can be directly in communication with each other so as to constitute a single bore. The transverse right section of each housing 20 is adapted to receive a radial stud 21, and, for example, is substantially elliptical in the example shown.

In a preferred embodiment, the cage 1 includes antirotation means 23 for co-operating with complementary means 24 provided on the jaws 17 of the manipulation forceps so as to prevent relative rotation between the cage 1 and the forceps 15 when the forceps are engaging the insert. In the example shown, these antirotation means 23 are constituted by a groove formed in each sagittal wall 2, 3 to open out into a corresponding housing 20 and extending therefrom to the outside face of the anterior transverse walls 4. As shown more particularly in FIG. 3, each groove 23 is substantially rectangular in right cross-section.

As can be seen more clearly in FIGS. 4 to 6, each insert-engaging jaw 17 is arranged to present complementary antirotation means 24 in the form of an arm or a bar having a free end carrying a radial stud 21 lying substantially in alignment with the other radial stud. Each arm 24 is of cross-section complementary to that of the groove 23 and is designed to be engaged at least in part in the groove 23 formed in a sagittal wall when each of the studs 21 is engaged in a complementary housing 20. According to a preferred characteristic of the invention, when the studs 21 are engaged in the housings 20 (FIG. 7), the outside faces of the jaws 17, i.e. the arms 24, extend substantially in line with the outside faces of the sagittal walls 2 and 3 so as to limit the approach path required for installing the cage.

Engaging the studs 21 in the housings 20 ensures that the cage is held securely and prevented from moving in translation, and the co-operation between the arms 24 and the grooves 23 prevents the cage from moving in rotation, in particular in a frontal direction. This ensures that the cage is completely prevented from moving relative to the jaws 17. It should be observed that the antirotation means 23, 24 could be be implemented in a different manner. For example, the housings 20 prismatic in shape for co-operating with studs of complementary shape.

According to a preferred characteristic, each jaw 17 is provided with a stop abutment 27 for coming into contact with the external face of the anterior transverse wall 4 of the cage when the studs 21 are engaged in the housings 20 so as to transmit forces that are exerted axially on the forceps. As can be seen more precisely in FIG. 4 to 6, each stop abutment 27 extends radially substantially parallel to the adjacent stud 21 which is connected to the stop abutment 27 via the locking arm 24. Each stop abutment 27 is preferably arranged on the jaw 17 so as to come into contact with the external face of the anterior wall of the cage substantially in line with the sagittal walls 2 and 3. Such a disposition provides the advantage of enabling pressure forces exerted on the end 30 of the forceps where the branches 16 join to be transmitted in such a manner as to facilitate insertion of the cage between the vertebrae. The branches 16 of the forceps are preferably made so as to be resilient and urge the jaws 17 permanently towards each other. In this respect, moving the branches 16 towards each other causes the jaws 17 to move apart because the branches cross over, whereas releasing the branches 16 automatically causes the jaws 17 to move towards each other.

SUSCEPTIBILITY OF INDUSTRIAL APPLICATION

The above-described cage 1 is particularly adapted to complying with the disk space defined between two vertebrae, e.g. cervical vertebrae. Complying with the anatomy of the intervertebral disk that is replaced by the cage 1 serves to encourage bone fusion between the vertebrae and to restore the static configuration of the spine. Furthermore, the cage 1 is made particularly simple to put into place by using the manipulation forceps 15 of the invention. Thus, from an anterior approach path to the cervical spine, resection is performed on the osteophytes, the disk is removed, and then the plane faces of the vertebrae are revivified. Thereafter, a cage 1 can be taken hold of by the forceps 15 by acting on the branches 16 to move the jaws 17 apart, then positioning the studs 21 in the housings 20, and then by acting on the branches so that the jaws 17 move towards each other, causing the studs 21 to penetrate into the housings 20 and causing the arms 24 to penetrate into the grooves 23. It should be observed that the grooves 23 are capable of providing a guidance function for the studs 21 which are thus brought up to the housings for insertion purupoises. In this position, the cage 1 is held completely securely relative to the forceps by the studs 21 being engaged in the housings 20 and by the arms 24 being engaged in the grooves 23, and also by the abutments 27 coming into contact against the anterior transverse wall 4. The cage 1 can be inserted into the disk space, with it being possible to apply thrust force to the end 30 of the forceps, should that be necessary. Pressing the branches 16 together to move the jaws 17 apart enables the studs 21 to be disengaged from the housings 20 so as to allow the forceps to be withdrawn.

The invention is not limited to the examples described and shown since numerous modifications can be made thereto without going beyond the ambit of the invention.

What is claimed is:

1. An intersomatic implant designed to be inserted in the disk space defined between two adjacent vertebrae, namely an overlying vertebra and an underlying vertebra, for the purpose of reestablishing the anatomic space between the vertebrae, the implant being in the form of a cage that is generally in the space of a rectangular block having at least two sagittal walls substantially parallel to a sagittal plane and interconnected at least by an anterior transverse wall and by a posterior transverse wall extending substantially parallel to a frontal plane, the walls defining between them an open volume for bone filler and presenting rims extending on one surface to define a first transverse face and on the opposite surface to define a second transverse face, wherein the first transverse face presents in the sagittal plane a first convex profile congruent with the sagittal anatomic profile of an overlying vertebra, and the first transverse face is defined in the frontal plane by a first substantially straight profile;

wherein the second transverse face presents in the frontal plane a second convex profile congruent with the frontal anatomic profile of an overlying vertebra, and the second transverse face presents in the sagittal plane a second substantially straight profile; and wherein the first and second convex profiles of each transverse face is defined by protuberances formed on the rims of the sagittal and frontal walls.

2. An implant according to claim 1, wherein the rims of the sagittal and frontal walls carry protuberances forming ridges extending parallel to one another and to the frontal plane.

3. An implant according to claim 1, further comprising at least one radio-opaque marker extending over at least a portion of the height of a wall.

4. An implant according to claim 1, further comprising two housings for receiving the jaws of a manipulation forceps, the housings extending substantially facing each other in a frontal direction perpendicular to the sagittal plane of the cage.

5. An implant according to claim 4, wherein each housing opens out at least to the external face of one of the sagittal walls.

6. An implant according to claim 4, wherein the walls are arranged to include antirotation means for co-operating with complementary means arranged on the jaws of the manipulation forceps so that, when the cage is engaged by the forceps, the cage is prevented from moving relative to the forceps.

7. An implant according to claim 6, wherein each housing opens to the sagittal walls in a respective groove extending to the external face of the anterior wall so as to consitute the antirotation means and so as to enable the jaws of a manipulation forceps to be inserted.

* * * * *